United States Patent
Williams et al.

(10) Patent No.: US 8,133,184 B2
(45) Date of Patent: Mar. 13, 2012

(54) CALIBRATION OF IN VIVO BLOOD PRESSURE SENSORS

(75) Inventors: Jonathan Williams, Montville, NJ (US); Shrenik Daftary, New York, NY (US); Robert Hamilton, Bergenfield, NJ (US)

(73) Assignee: Datascope Investment Corp., Mahwah, NJ (US)

( * ) Notice: Subject to any disclaimer, the term of this patent is extended or adjusted under 35 U.S.C. 154(b) by 0 days.

(21) Appl. No.: 12/803,853

(22) Filed: Jul. 8, 2010

(65) Prior Publication Data

US 2010/0312126 A1    Dec. 9, 2010

Related U.S. Application Data

(63) Continuation of application No. 11/494,973, filed on Jul. 27, 2006, now Pat. No. 7,771,362.

(60) Provisional application No. 60/704,262, filed on Aug. 1, 2005.

(51) Int. Cl.
*A61B 5/02* (2006.01)

(52) U.S. Cl. ........ 600/486; 600/485; 600/500; 600/504; 600/435

(58) Field of Classification Search .......... 600/485, 600/486, 500, 504, 505, 435
See application file for complete search history.

(56) References Cited

U.S. PATENT DOCUMENTS

| | | | | |
|---|---|---|---|---|
| 4,685,446 A | * | 8/1987 | Choy | 600/18 |
| 4,878,898 A | * | 11/1989 | Griffin et al. | |
| 5,133,358 A | * | 7/1992 | Gustafson et al. | 600/488 |
| 5,158,529 A | | 10/1992 | Kanai | |
| 5,458,571 A | * | 10/1995 | Lampropoulos et al. | |
| 5,788,642 A | * | 8/1998 | Hamatake et al. | |
| 5,873,835 A | | 2/1999 | Hastings et al. | |
| 5,913,814 A | * | 6/1999 | Zantos | 600/18 |
| 6,120,457 A | * | 9/2000 | Coombes et al. | 600/486 |
| 7,134,341 B2 | * | 11/2006 | Girmonsky et al. | 73/579 |
| 2003/0101800 A1 | * | 6/2003 | Williams | 73/40 |
| 2004/0097813 A1 | * | 5/2004 | Williams | 600/485 |

* cited by examiner

*Primary Examiner* — Patricia Mallari
*Assistant Examiner* — Michael D'Angelo
(74) *Attorney, Agent, or Firm* — Jarrett Silver

(57) ABSTRACT

A method for performing an in-vivo calibration of a blood pressure sensor that is associated with a balloon of an in-vivo balloon system, the sensor and balloon being associated such that the sensor is in-vivo when the balloon is in-vivo. The balloon is inflated so that a gas pressure in the balloon system is indicative of a patient's blood pressure. The patient's blood pressure is monitored through two channels, the gas pressure and the sensor. The blood pressure measurements obtained by monitoring the gas pressure are used as reference, or "true," blood pressure measurements to determine a mathematical relationship between blood pressure measurements obtained through the sensor and the reference blood pressure measurements. In this manner, future blood pressure measurements obtained through the sensor can be modified according to the mathematical relationship to generate calibrated blood pressure measurements.

7 Claims, 16 Drawing Sheets

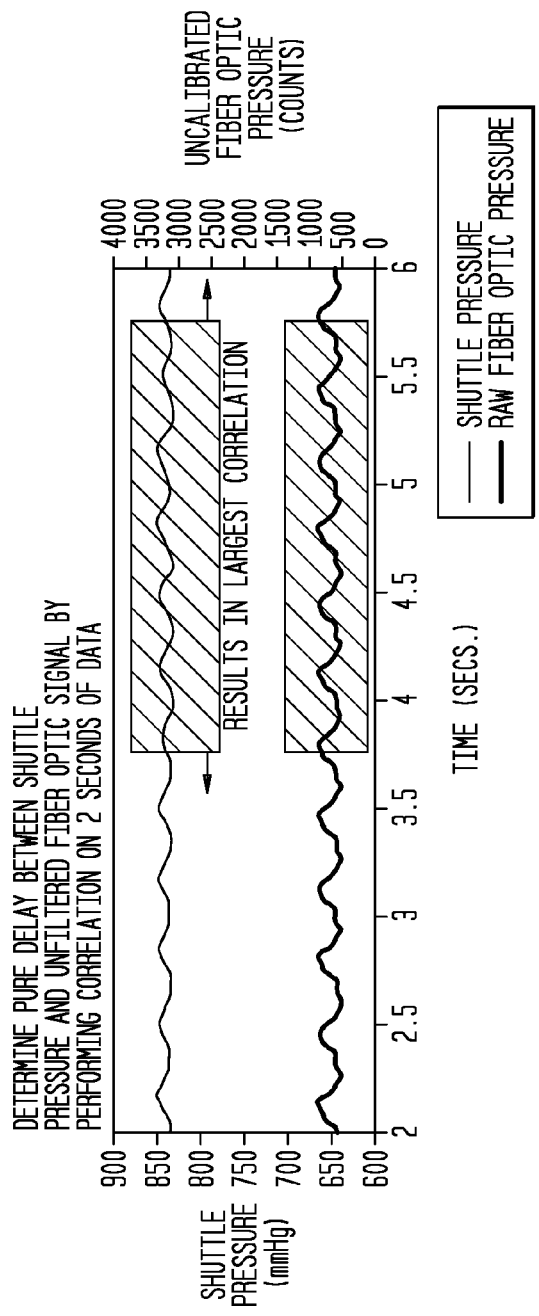
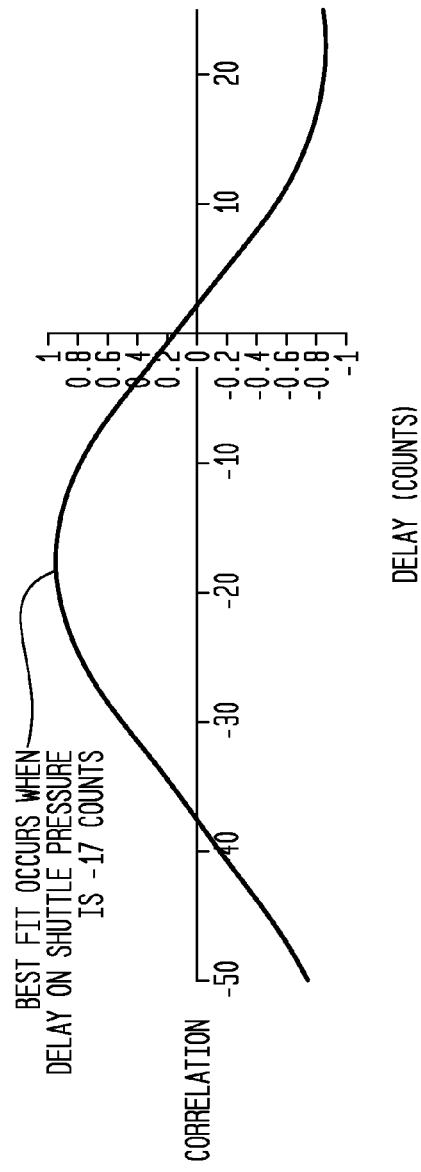

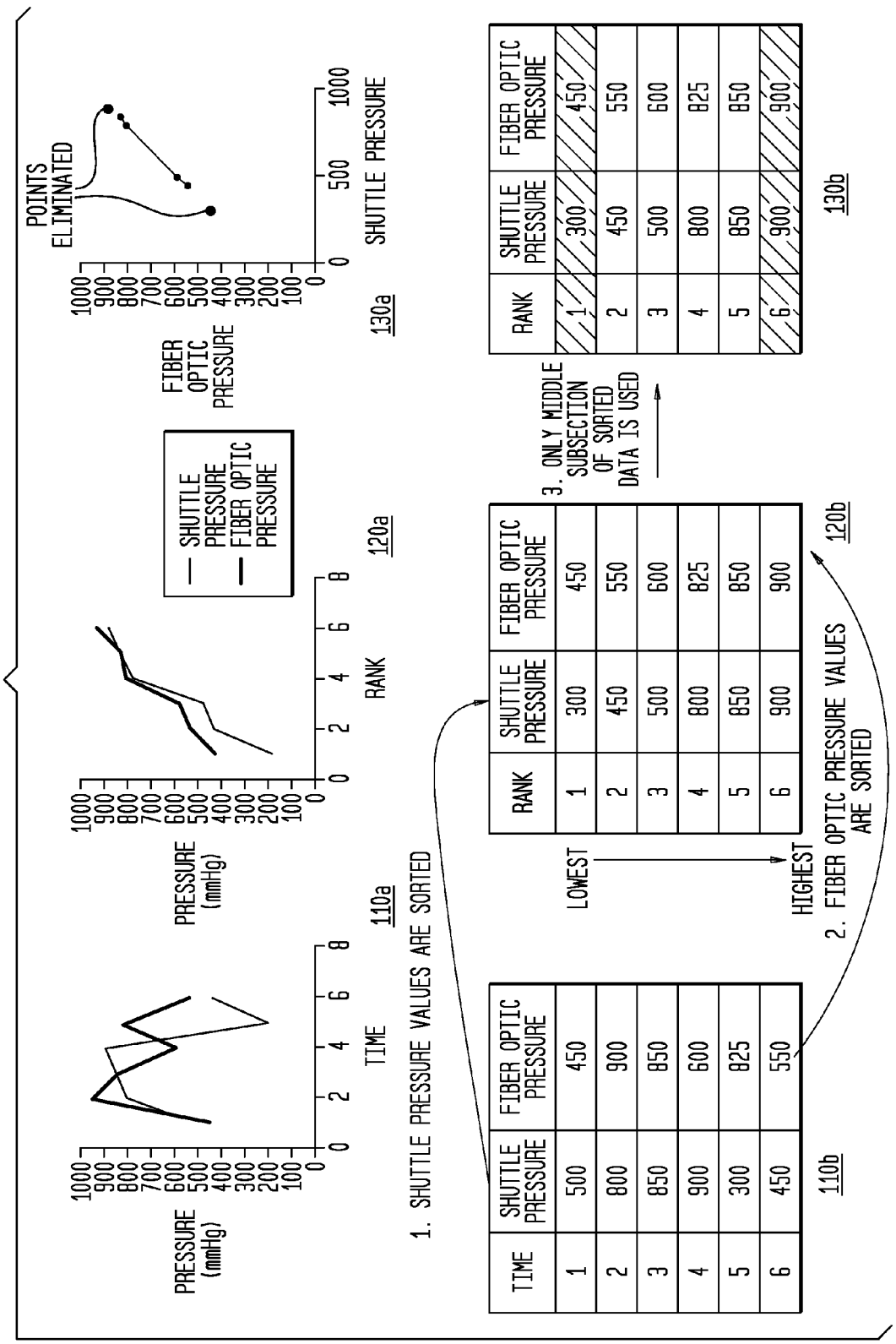

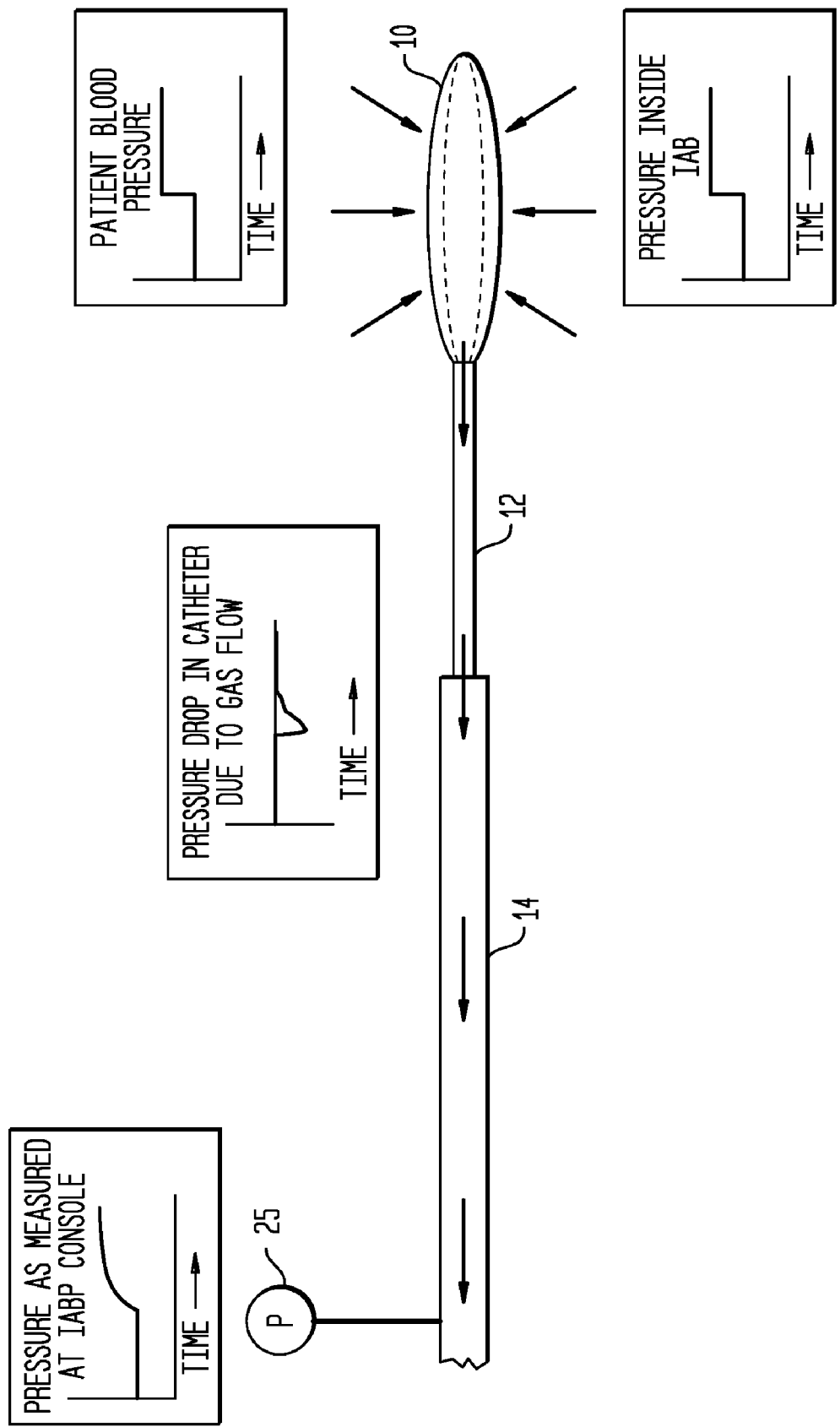

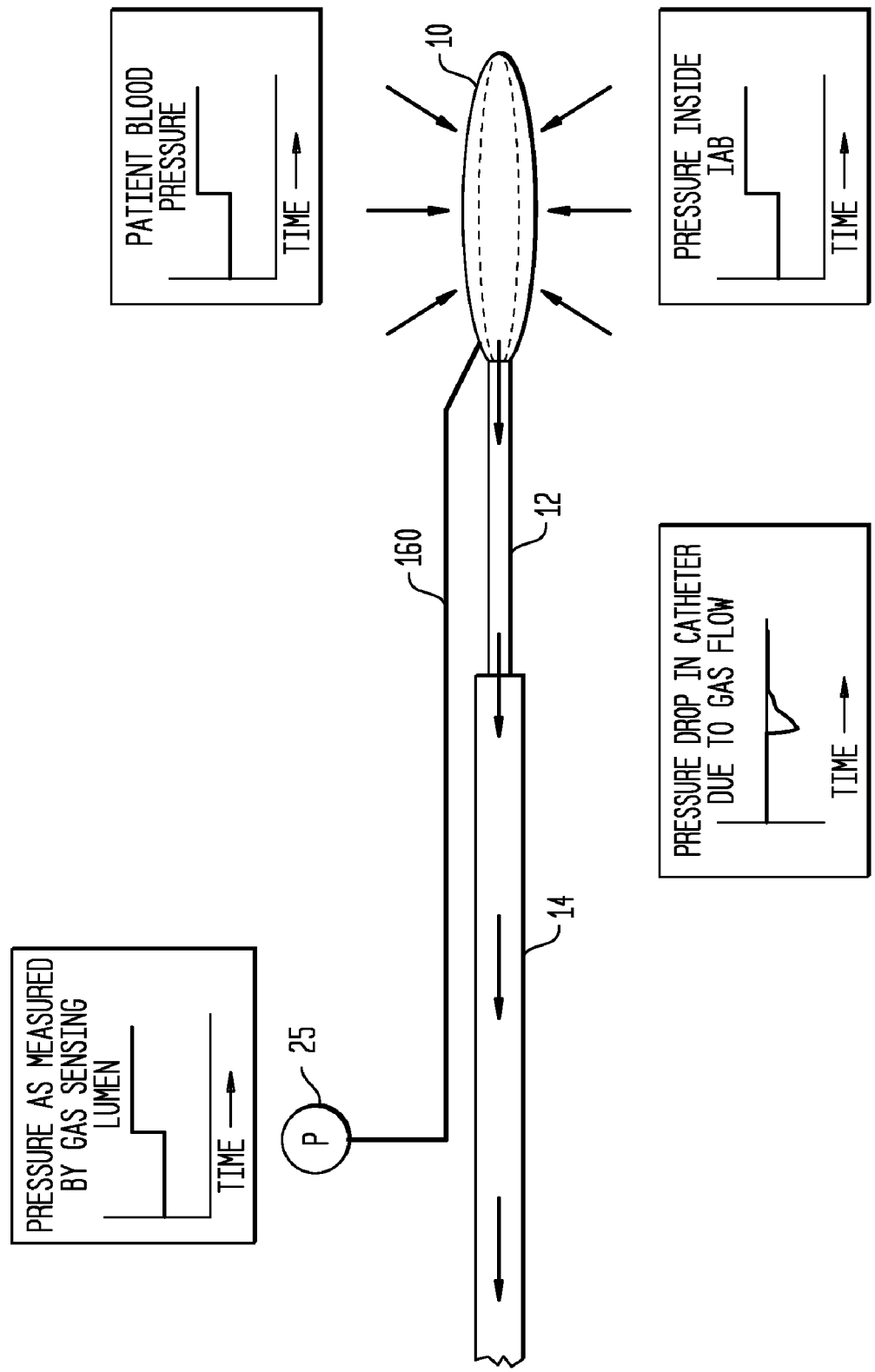

CALIBRATION OF IN VIVO BLOOD PRESSURE SENSORS

CROSS-REFERENCE TO RELATED APPLICATION

The present application is a continuation of U.S. patent application Ser. No. 11/494,973, filed Jul. 27, 2006, which claims benefit of U.S. Provisional Application No. 60/704,262, filed Aug. 1, 2005, the disclosures of which are hereby incorporated by reference herein.

FIELD OF THE INVENTION

The present invention relates generally to calibrating blood pressure sensors intended for in-vivo use while such sensors are in-vivo, and more particularly, to calibration of in-vivo blood pressure sensors that are associated with a balloon or balloon-like construct that is intended for in-vivo use. Still more particularly, the present invention relates to calibrating in-vivo blood pressure sensors that are associated with an in-vivo balloon, or balloon-like construct, by using readings of gas pressure within the balloon or balloon-like construct.

BACKGROUND OF THE INVENTION

In the practice of medicine there are many instances in which accurate measurement of patient blood pressure is required. In some instances, it is necessary to obtain accurate blood pressure measurements from particular locations within a patient's body, or "in-vivo." Among those instances in which it is necessary to obtain accurate in-vivo blood pressure measurements are procedures involving the use of an in-vivo balloon or in-vivo balloon-like construct. (In the interest of brevity the term "balloon" will be used throughout this description to denote balloons and balloon-like constructs.)

One type of procedure that uses an in-vivo balloon is intra-aortic balloon (IAB) therapy. By way of illustration, further background will be provided in the context of IAB therapy.

Intra-aortic balloon pump therapy is frequently prescribed for patients who have suffered a heart attack or some other form of heart failure. In such therapy, a thin balloon is inserted through an artery into the patient's aorta. The balloon is connected through a series of tubes to a complex drive apparatus which causes the balloon to inflate and deflate repeatedly in time with the patient's heartbeat, thereby removing some of the load from the heart and increasing blood supply to the heart muscle during the therapy period.

The inflation/deflation apparatus supplies positive pressure for expanding the balloon during an inflation cycle and negative pressure for contracting the balloon during a deflation cycle. An IAB apparatus is shown schematically in FIG. 1. In the FIG. 1 apparatus, an intra-aortic balloon (IAB) 10 is surgically inserted into a patient's aorta and is connected through a catheter 12 having a small diameter lumen, a connector 11, and an extender 14 having a relatively large diameter lumen to a pneumatic isolator 18 divided by a pliant membrane 20 into a primary side 22 and a secondary side 24. Accordingly, all elements to the left of membrane 20 in FIG. 1 are referred to as being on the "primary side" of the FIG. 1 apparatus, and all elements to the right of membrane 20 in FIG. 1 are referred to as being on the "secondary side" of the FIG. 1 apparatus.

The entire volume between membrane 20 and balloon 10 is completely filled with a gas, such as helium, supplied by a gas source 26. The gas source is coupled to the secondary side of the isolator via a fill/purge line 15. A gas pressure sensor 25 is provided for monitoring the gas pressure within the secondary side of the IAB apparatus. For purposes of discussion, the gas present within the secondary side of the IAB system is referred to as the "shuttle gas." Accordingly, pressure sensor 25 is the "shuttle gas pressure sensor" and it measures "shuttle gas pressure."

A positive pressure source 28 is connected through a solenoid valve 30 to the input or primary side 22 of isolator 18. Similarly, a negative pressure source 32 is connected through a solenoid valve 34 to the input or primary side 22 of isolator 18. The primary side 22 of isolator 18 is also connected through a solenoid valve 36 to a vent or exhaust port 38. In such systems, the isolator, gas source, negative and positive pressure sources, vent port and their associated valves together comprise a reusable drive unit, and the extender, catheter and balloon are disposable so as to accommodate sterility concerns.

During an inflation cycle, solenoid valve 30 is opened to permit positive pressure from positive pressure source 28 to enter primary side 22 of isolator 18. This positive pressure causes membrane 20 to move toward secondary side 24, thereby forcing the shuttle gas in the secondary side to travel toward and inflate balloon 10. For deflation, solenoid valve 30 is closed and solenoid valve 36 is opened briefly to vent the gas from primary side 22 to atmosphere, after which valve 36 is closed. Solenoid valve 34 is then opened, whereupon negative pressure source 32 creates a negative pressure on the primary side 22 of isolator 18. This negative pressure pulls membrane 20 toward primary side 22, whereby the shuttle gas is drawn out from the balloon.

Maximum patient benefit is achieved when the timing of IAB inflation and deflation is correct. To meet this requirement, the patient's blood pressure waveform must be accurately monitored. The monitored signal is then analyzed for key cardiac events.

Accordingly, the IAB system as shown in FIG. 1 includes a pressure sensor 40 proximal to the front end of the balloon for the purpose of monitoring a patient's blood pressure during IAB therapy. Sensor 40 can be a fiber optic sensor that measures pressure by observing how light is reflected from a diaphragm which moves in response to pressure changes. The optical signal generated by sensor 40 is passed back to a monitor outside of the patient's body via a fiber optic line 13 that passes through the balloon 10, catheter 12 and connector 11 (connector 11 being a pneumatic and fiber optic connector suitable for accommodating both a fiber connection and a pneumatic connection between the catheter and extender). The optical "pressure" signal transmitted through line 13 is converted into an electrical signal by converter module 17.

SUMMARY OF THE INVENTION

The present invention provides a method for performing an in-vivo calibration of a blood pressure sensor that is associated with an in-vivo balloon system, the sensor and balloon being associated such that the sensor is in-vivo when the balloon is in-vivo. The method involves partially inflating the balloon so that the shuttle gas pressure in the system is indicative of a patient's blood pressure, monitoring the patient's blood pressure by observing the shuttle gas pressure while at the same time monitoring the patient's blood pressure through the sensor, and using blood pressure measurements obtained by monitoring the shuttle gas pressure as reference, or "true," blood pressure measurements to determine a mathematical relationship between blood pressure measurements obtained through the sensor and the reference blood pressure measurements. After determining a mathematical relationship between the blood pressure measurements obtained through the sensor and the reference, or "true," blood pressure measurements, the relationship can be used to adjust future measurements obtained from the sensor to thereby generate calibrated sensor measurements.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIGS. 5A and 5B are graphs showing how a correlation process is used to determine the relative time delay between blood pressure measurements obtained from an IAB system balloon and blood pressure measurements obtained from a fiber optic sensor associated with the balloon.

FIG. 9A provides a simplified example of data sorting and data exclusion processes in accordance with the invention.

FIG. 11 shows several graphs superimposed on an IAB system similar to that of FIG. 1 to illustrate how the pressure changes at various points in the system when the system experiences a "step" in blood pressure.

FIG. 14 shows an IAB system that includes a gas lumen which couples a shuttle gas pressure sensor directly to the IAB, and includes several graphs illustrating how the pressure changes at various points in the FIG. 14 system when the system experiences a "step" in blood pressure.

DETAILED DESCRIPTION

Figure 1:
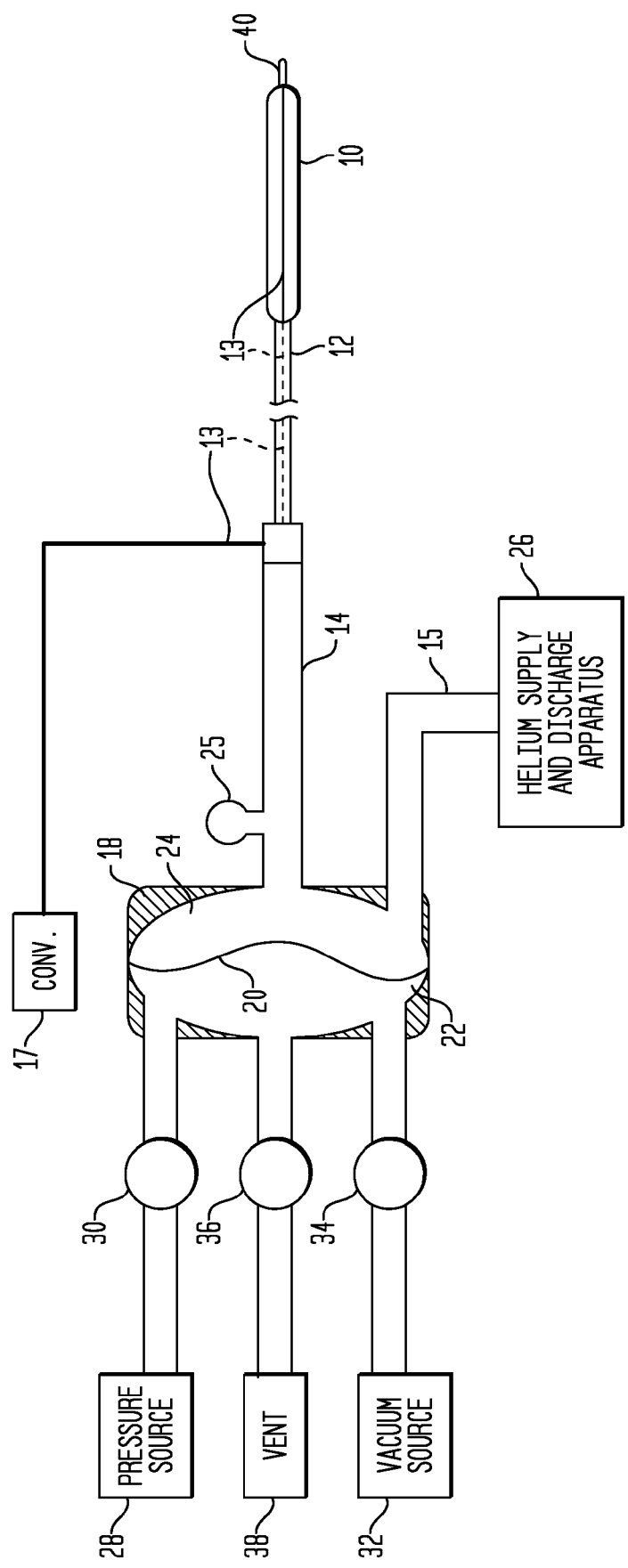
FIG. 1 is a highly schematic view showing an intra-aortic balloon system.

It has been recognized that in order to obtain accurate blood pressure measurements from in-vivo blood pressure sensors it is necessary to calibrate such sensors individually and repeatedly. One reason calibration is necessary is that the sensors are subject to inconsistencies in their manufacture which cause their performance to vary from sensor-to-sensor. Another reason is that the performance of a sensor varies over time as the sensor is subjected to environmental stress. Thus, even if a sensor is calibrated prior to leaving the factory, it requires recalibration from time-to-time to account for environmental stress.

In prior systems, the calibration process is initiated by a clinician who adjusts the "zero point" of the sensor by exposing the sensor to atmospheric pressure before it is placed in the patient and then applying a correcting offset to compensate for any amount that the sensor reading deviates from atmospheric pressure. For example, if the sensor reads 10 mmHg (gauge pressure) when exposed to atmospheric pressure, then a 10 mmHg correcting offset is applied. That is, 10 mmHg is subtracted from the sensor reading to "zero" the sensor. This type of calibration has several drawbacks. One drawback is that after the sensor is inserted into the patient, re-zeroing is not practical, since re-zeroing requires the removal of an already placed sensor. Another drawback is that the application of a fixed compensating offset does not account for "drift" (or "variability or errors") in the sensor's scale factor (also called "sensitivity" or "gain"). More specifically, the sensor error may be different at pressures other than atmospheric so that the offset necessary to achieve an accurate reading when the sensor is exposed to atmospheric pressure may not yield an accurate reading when the sensor is exposed to a different pressure.

Accordingly, the present invention provides a scheme for calibrating an in-vivo blood pressure sensor as frequently as necessary and using a dynamic blood pressure waveform. The calibration can be performed in-vivo during, for example, an IAB therapy session without any operator intervention or removal of the IAB. By using a dynamic blood pressure waveform for calibration, the invention corrects for drift of the sensor's offset and scale factor.

The present invention relates to calibrating in-vivo blood pressure sensors that are associated with an in-vivo balloon by using measurements of gas pressure within the balloon. For purposes of clarity of presentation, the detailed description of the invention will focus on the IAB therapy implementation of the invention. In view of such detailed description, one skilled in the art of the invention can readily apply the invention in other in-vivo contexts. Further, the detailed description will focus on implementation of the invention in an IAB system like that shown in FIG. 1. In view of the detailed description with reference to FIG. 1, one skilled in the art of the invention can readily apply the invention in IAB systems other than that depicted in FIG. 1. For example, after reading the detailed description, one skilled in the art will be able to apply the invention to an IAB system that uses a bellows in lieu of some or all of the drive unit elements depicted in FIG. 1.

In a preferred embodiment of the invention, calibration of a fiber optic sensor proximal an intra-aortic balloon is performed in-vivo. Of course, while the calibration of a fiber optic sensor is described in detail, the invention may be applied to any type of in-vivo sensor, including any type of electronic sensor, and any type of opto-electronic sensor. It is preferable that calibration is performed at the initiation of intra-aortic balloon ("IAB") therapy and as needed based on elapsed time from the most recent calibration, patient conditions (e.g. the patient's systolic and diastolic pressure, and the patient's body temperature), and/or environmental changes.

During the calibration process, pumping is suspended for a brief interval while calibration data is collected. While pumping is suspended, simultaneous readings of the patient's aortic blood pressure are obtained from two pressure measurement channels. One channel conveys readings from the fiber optic pressure sensor 40 located at the tip of the IAB. The other channel conveys readings from the shuttle gas pressure sensor 25.

Normally, during pumping, the shuttle gas channel measures the pressure of the gas used to inflate and deflate the balloon. However, when conditions are correct, measurements of patient blood pressure can be obtained from this sensor. These measurements require that: 1) pumping is suspended, and 2) the balloon is held in a partially inflated state while data is collected, i.e., the balloon's membrane is flaccid while data is collected. When the balloon is in a partially inflated state, the pressure of the gas within the IAB is identical to the pressure on its exterior, i.e., the pressure of the gas can be used as a "surrogate" for patient blood pressure.

The fidelity of the calibration process is optimized when the IAB is inflated to a "target displacement volume." Typically, this target displacement volume for adult IABs is 10 cc.

After calibration data is collected, the IAB is refilled to its "normal" inflation volume, and pumping resumes. In the background, the collected calibration data is processed by an algorithm that calibrates the fiber optic sensor. The calibration process assumes that the shuttle gas pressure sensor 25 is accurate and uses its measurements as a reference to calibrate the fiber optic sensor 40. Once calibration is complete, patient blood pressure measurements are derived solely from the corrected measurements from the fiber optic sensor and pumping resumes.

Having provided an overview of the calibration process in accordance with the invention, the process will now be discussed in more detail.

Figure 2:
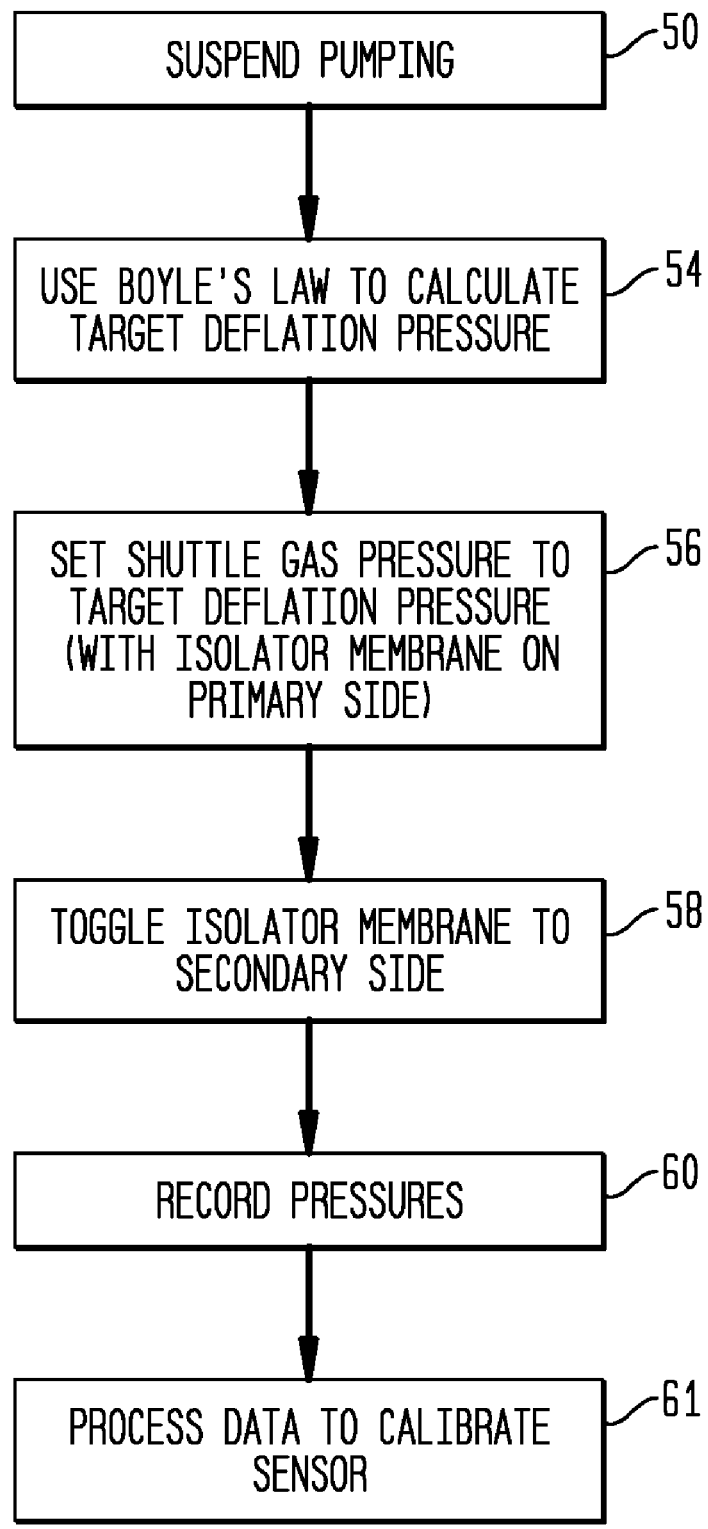
FIG. 2 is a flow chart showing how the IAB system of FIG. 1 is calibrated in accordance with the present invention.

FIG. 2 is a flow chart showing how the IAB system of FIG. 1 is calibrated in accordance with the present invention. The calibration process initially involves setting the IAB system such that the balloon can be used to provide reference, or "true," blood pressure readings. The first step in setting up the IAB system to provide balloon based blood pressure measurements is the suspension of pumping (step 50). Following the suspension of pumping, the IAB is filled to the target displacement volume for calibration. Achieving the correct target displacement volume is critical since the balloon must be kept in a flaccid state throughout the period in which calibration data is collected. If the balloon is allowed to completely inflate or deflate during the time when calibration data is collected, then the blood pressure readings obtained through the shuttle gas pressure sensor 25 will be unusable for calibration.

The procedure for achieving the target displacement volume will be discussed in the context of an IAB system in which the volume of gas in the balloon can not be directly measured. Further, it is presumed that the volume of gas present within the secondary side of the IAB system can not be directly measured.

In order to properly adjust the volume of gas in the secondary side of the IAB system such that the target displacement volume is achieved, Boyle's law is relied upon. More specifically, Boyles law (P1*V1=P2*V2) is used to relate the pressure (P1) and volume (V1) of the shuttle gas under a first condition (deflation) to the pressure (P2) and volume (V2) of the shuttle gas under a second condition (partial inflation). By allowing P2 to denote the shuttle gas pressure when the target displacement volume is achieved, solving Boyle's law for P1 determines the "target deflation pressure," that is, the pressure necessary to achieve the target displacement volume.

In practice, the first condition for calculation of target deflation pressure is that of the membrane 20 being on the primary side of the isolator 18 and the balloon 10 being completely deflated. The second condition is that of the membrane being on the secondary side of the isolator and the balloon being filled to its target displacement volume. Given the two conditions and using the term "dead volume" to denote the total volume of gas present in the combination of sensor 25, extender 14, catheter 12 and fill/purge line 15, the target deflation pressure is computed according to the following implementation of Boyle's law: P1=target deflation pressure; V1=isolator volume+dead volume; P2=load pressure; and V2=target displacement volume+dead volume (step 54). Using these values in P1*V1=P2*V2 and solving for target deflation pressure yields: target deflation pressure=(load pressure*(target displacement volume+dead volume))/(isolator volume+dead volume). It is noted that use of Boyle's law in this manner assumes that the target displacement volume, isolator volume, and dead volume have been determined. A target displacement volume of 10 cc and an isolator volume of 73.5 cc have been used in an illustrative system. A technique for determining the dead volume is disclosed below.

Dead volume is also calculated through use of Boyle's law. In this case, the two conditions used for dead volume calculation are: (1) membrane on primary side of isolator, balloon completely deflated; and (2) membrane on secondary side of isolator, balloon completely deflated. Moreover, to accurately perform dead volume calculation, three requirements must be met. First, to ensure that the membrane 20 remains positioned against the primary side of the isolator in the first condition, the gas pressure in the primary side of the IAB system must be less than the shuttle gas pressure. Second, a shuttle gas pressure must be set such that the balloon will remain deflated throughout the dead volume measurement. Third, the volume of the isolator must be known.

Figure 3:
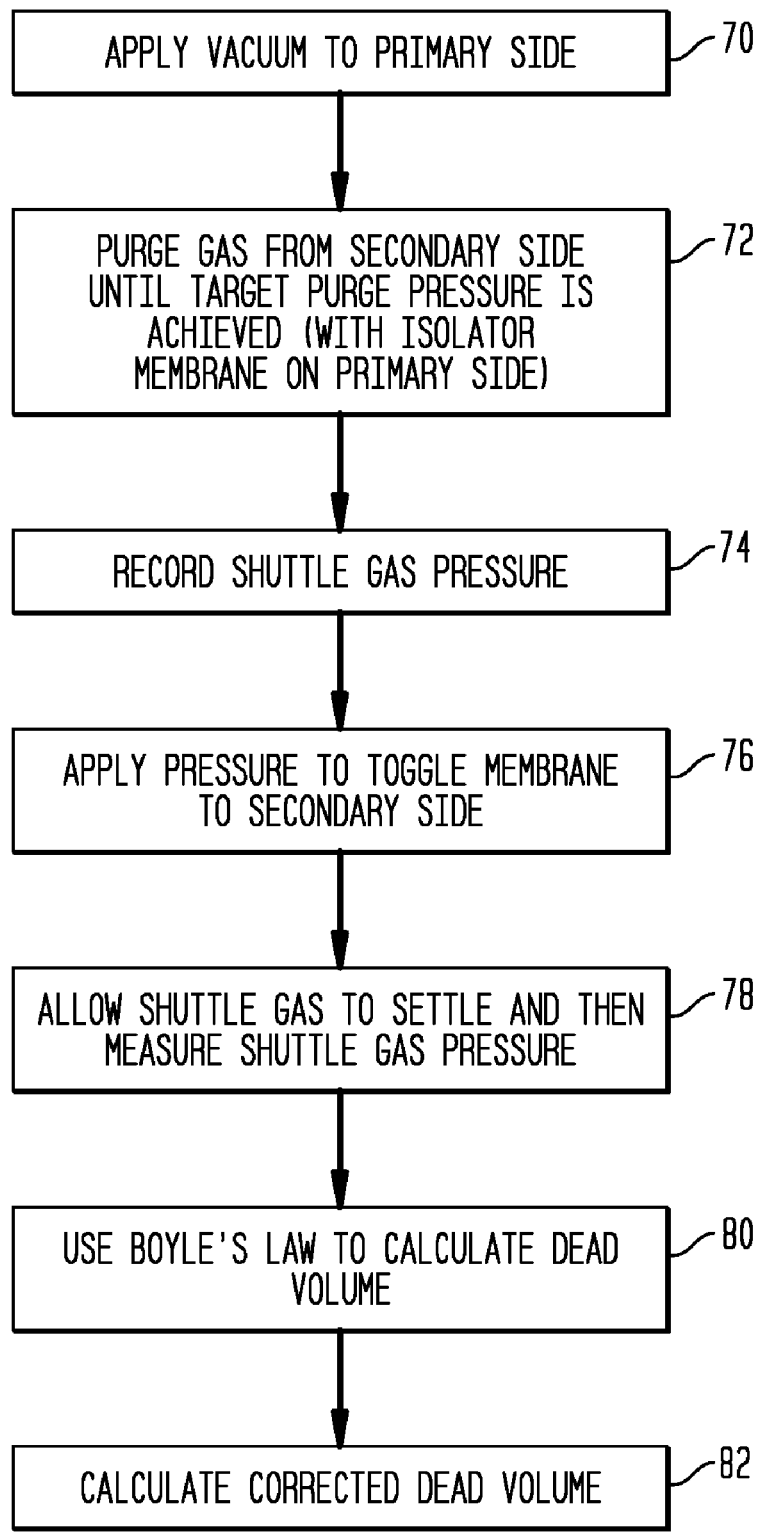
FIG. 3 is a flow chart showing how the dead volume of an IAB system is calculated in accordance with the present invention.

Dead volume calculation will be discussed with reference to the flow chart of FIG. 3. The first step in dead volume calculation is to apply a vacuum to the primary side of the IAB system (step 70). The vacuum is preferably less than 150 mmHg absolute. The 150 mmHg value is selected because it ensures that the membrane will be positioned on the primary side of the system during the following operations. First, shuttle gas is purged from the secondary side of the system until the gas in the secondary side reaches a "target purge pressure" (step 72). The target purge pressure is preferably selected to be 200 mmHg absolute (+/−10 mmHg) because such level is greater than the vacuum level required by an illustrative IAB system to complete an "autofill" (refill of the shuttle gas to its default level), yet ensures that the balloon will not inflate when membrane 20 is toggled to the secondary side.

Next, after purging the secondary side of the system and toggling the membrane to the primary side, the shuttle gas pressure is recorded (P1) (step 74). In an ideal system, the recorded shuttle gas pressure will equal the desired target purge pressure. Nevertheless, in the interest of precision the "P1" pressure used in the dead volume calculation is the pressure read from the gas pressure sensor and is not assumed to be equal to desired target purge pressure. In this manner, it is possible to account for inaccuracies inherent in the purging process.

Next, positive pressure is applied to the membrane from the primary side so that it toggles to the secondary side (step 76). After a period in which the shuttle gas pressure is allowed to equilibrate, then the shuttle gas pressure is measured again (P2) (step 78). When measuring P1, the volume (V1) is equal to the isolator volume plus the dead volume. When measuring P2, the volume (V2) is equal to the dead volume. Since P1, P2 and the isolator volume are known, the dead volume can be calculated using Boyle's law of $P1*V1=P2*V2$ (step 80). That is, dead volume can be calculated by solving the equation $P1*(\text{isolator volume}+\text{dead volume})=P2*(\text{dead volume})$, or dead volume=$(P1*(\text{isolator volume}))/(P2-P1)$. However, the resulting dead volume must be corrected to compensate for the elasticity of the system's pneumatic tubing.

The IAB system's pneumatic tubing expands and/or contracts as the pressure differential between the inside of the tubing and the outside of the tubing changes. In the FIG. 1 configuration, since the extender, catheter and purge/fill line are not rigid, their volumes vary as the pressure differential varies. The internal pressure on the tubing relative to the external pressure is negative while the dead volume calculation is made. The internal pressure on the tubing relative to the external pressure is positive while the balloon is partially inflated. Therefore, compensation for expansion of the tubing is required. Preferably, a tubing expansion constant is used to compute the increased volume due to tubing expansion. By way of illustration it is noted that in a test case the average observed expansion constant for extension catheters was 0.0042 cc/mmHg.

The expansion/contraction of the system's pneumatic tubing is negligible when the shuttle gas pressure changes between "P1" of step 74 and "P2" of step 78. However, the expansion/contraction should be considered when the shuttle gas pressure changes between the vacuum of steps 74-78 and the patient's blood pressure.

Thus, once the tubing expansion constant is determined, the corrected dead volume is calculated from the equation: corrected dead volume=dead volume+(tubing expansion constant*(load pressure−P2)), wherein the load pressure is average blood pressure of the patient (step 82), wherein P2 is the pressure measured during the second condition of the dead volume calculation (i.e. the pressure measured in step 78). The load pressure is preferably assumed to be 150 mmHg gauge pressure prior to the first calibration and is equal to the patient's mean blood pressure following the first calibration. The pressure "P2" of step 78 is used without consideration of the tubing expansion constant since the tubing expansion that occurs when proceeding from steps 74 to 78 is negligible.

After calculating the corrected dead volume, Boyle's law is used to calculate the "target deflation pressure." The target deflation pressure is the shuttle gas pressure that must exist when the balloon is deflated and the membrane is against the primary side of the isolator, such that toggling the membrane to the secondary side of the isolator will fill the balloon to the target displacement volume. Once, the corrected dead volume is calculated, the target deflation pressure is computed according to the following implementation of Boyle's law: P1=target deflation pressure; V1=isolator volume+corrected dead volume; P2=load pressure; and V2=target displacement volume+corrected dead volume (step 54). Using these values in $P1*V1=P2*V2$ and solving for target deflation pressure yields: target deflation pressure=(load pressure*(target displacement volume+corrected dead volume))/(isolator volume+corrected dead volume).

It should be noted that the dead volume needs to be determined only once for the given combination of sensor 25, extender 14, catheter 12 and fill/purge line 15 since the dead volume is a system constant. Thus, the dead volume does not need to be determined each time the sensor is calibrated.

In any case, once the target deflation pressure has been calculated, shuttle gas is added and/or removed from the secondary side of the system with the membrane on the primary side until the shuttle gas pressure equals the target deflation pressure (step 56). The membrane is then fully toggled to partially inflate the balloon (step 58). Upon toggling of the membrane, the balloon is ready to be used to measure blood pressure. Once the system has been set up to measure blood pressure via the balloon, balloon-based blood pressure measurements and fiber optic blood pressure measurements are recorded for a period of time (step 60). The recorded measurements are then processed to calibrate the fiber optic sensor (step 61).

Before discussing how the recorded measurements are processed, it is important to note the differences between the "shuttle gas pressure channel," through which the balloon-based blood pressure measurements are obtained, and the "fiber optic channel," through which the fiber optic blood pressure measurements are obtained. The frequency response of the shuttle gas channel differs significantly from that of the fiber optic channel. The fiber optic pressure sensor is in direct contact with the patient blood and directly measures patient blood pressure. The pressure signal is transmitted optically and processed by low delay, high bandwidth circuitry. For this reason, it has high bandwidth, low time delay and good fidelity. The shuttle gas channel measures patient blood pressure indirectly via a pneumatic transmission pathway. The pneumatic transmission process delays the pressure signal and suppresses its higher frequencies. The effect of this transmission process can be approximated by a time delay and a low pass filter.

Figure 3A:
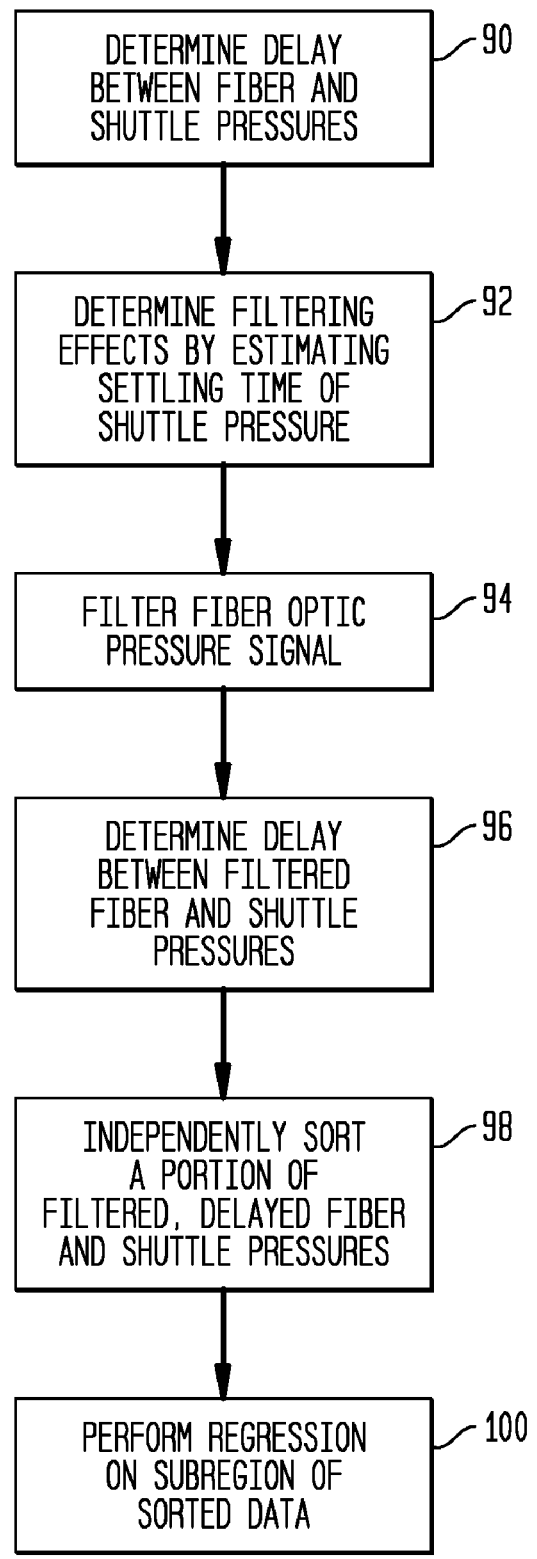
FIG. 3A is a flow chart showing how blood pressure measurements obtained via an IAB system balloon and blood pressure measurements obtained from an uncalibrated fiber optic sensor associated with the balloon are processed to generate a mathematical relationship between the two types of measurements.

Referring now to FIG. 3A, there is shown a flow chart showing how blood pressure measurements obtained via an IAB system balloon and blood pressure measurements obtained from an uncalibrated fiber optic sensor associated with the balloon are processed to generate a mathematical relationship between the two types of measurements. The steps depicted in FIG. 3A will be described briefly with references to FIG. 3A, and then in more detail with references to FIGS. 4-10.

As can be seen from FIG. 3A, the first step in generating a mathematical relationship between uncalibrated fiber optic sensor measurements and balloon-based measurements is to determine the delay between the fiber optic and balloon-based measurements (step 90). Next, a determination is made of the filtering effects of the shuttle gas system upon the balloon-based measurements (step 92), the fiber optic measurements and the balloon-based measurements being shifted in time to account for the delay computed in step 90. After determining the filtering effects of the shuttle gas system, the fiber optic measurements are filtered in a way that mimics the filtering effects of the shuttle gas system (step 94). In this manner, the process of FIG. 3A can account for any differences between the balloon-based measurements and the fiber optic measurements that are caused solely by the filtering effects of the shuttle gas system. The next step is to determine the delay between the filtered fiber optic measurements and the balloon based measurements (step 96) so that such delay can be accounted for in a comparison of the filtered fiber optic measurements and the balloon-based measurements. Next, a portion of the filtered fiber optic measurements, as shifted according to the delay computed in step 96, is sorted along with a corresponding portion of balloon-based measurements (step 98). It is important to note that the term "sorting" refers to listing measurements in order of their value, from lowest to highest; although an option is to list the measurements from highest to lowest. Finally, a regression procedure is performed on a sub-region of the sorted measurements of step 98 to generate the mathematical relationship between the sorted fiber optic measurements and the sorted balloon-based measurements (step 100). Having provided an overview of the steps involved in the process of generating a mathematical relationship between uncalibrated fiber optic sensor measurements and balloon-based measurements, the process will now be described in detail with references to FIGS. 4-10.

Figure 4:
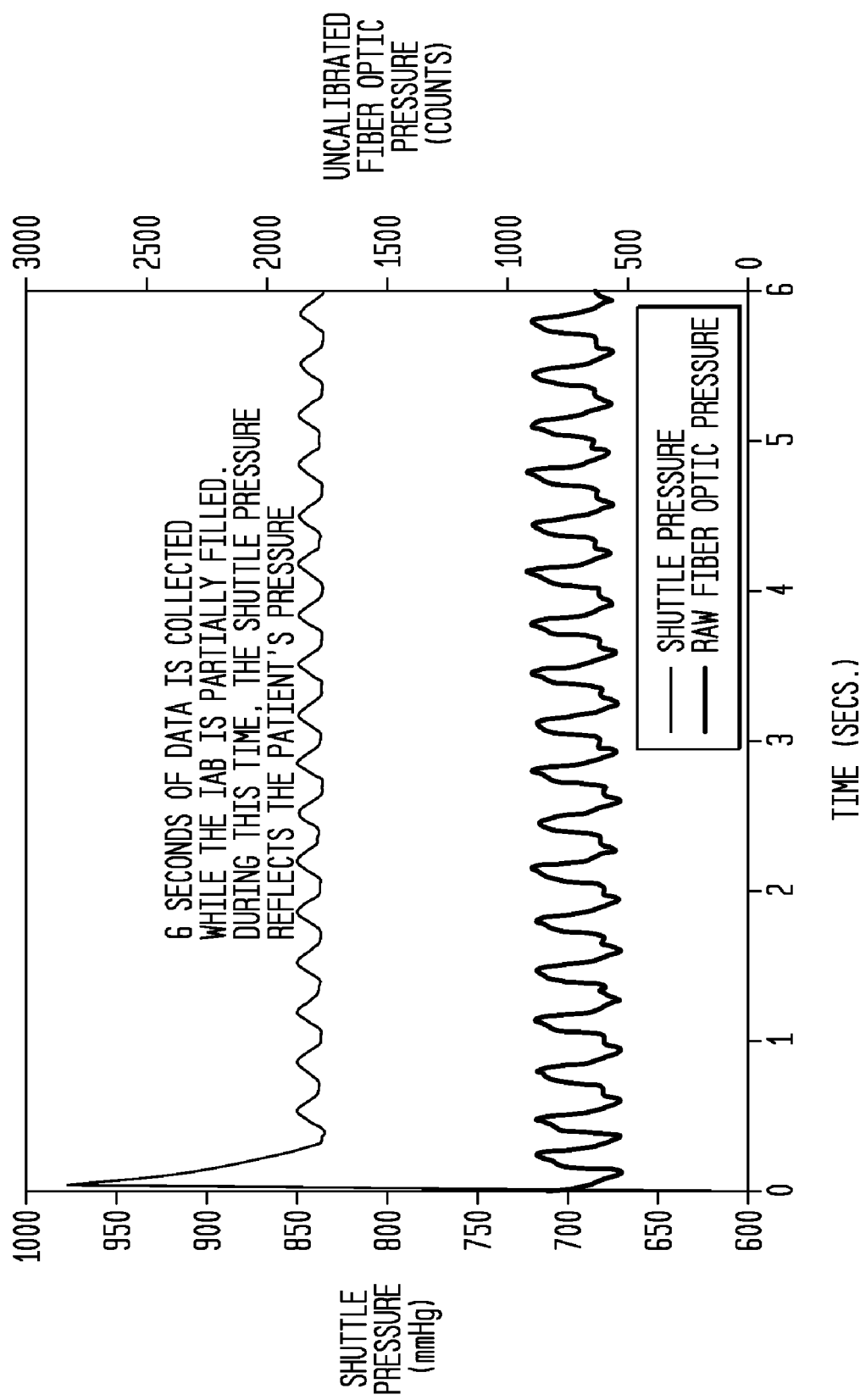
FIG. 4 is a graph showing blood pressure measurements obtained via an IAB system balloon and blood pressure measurements obtained from an uncalibrated fiber optic sensor associated with the balloon.

FIG. 4 is a graph showing simultaneous blood pressure measurements obtained via an IAB system balloon and blood pressure measurements obtained from a fiber optic sensor associated with the balloon. Preferably, the data is collected using periodic digital samples for both the blood pressure as measured through the balloon and the blood pressure as measured by the fiber optic sensor. The samples are collected at a uniform sampling rate, or "sampling frequency," that is equal to 1/(the period between samples). A sample rate of 250 Hz was used.

At time t=0 seconds, the membrane 20 is toggled to partially inflate the balloon. The partial inflate results in a momentary spike that can be observed on the shuttle pressure sensor. A fraction of a second after the membrane is toggled the shuttle pressure stabilizes. In an illustrative embodiment, all 6 seconds of data shown in FIG. 4, both balloon-based data and fiber optic sensor data, are collected for use in calibration.

FIGS. 5A and 5B are graphs showing how a correlation process is used to determine the relative delay between the blood pressure measurements obtained through the IAB system balloon and the blood pressure measurements obtained from the fiber optic sensor. FIG. 5A shows seconds two through six of the data collected for both the blood pressure as measured through the balloon and the blood pressure as measured by the fiber optic sensor. Since the blood pressure incident on the balloon must propagate through the shuttle gas and associated shuttle gas apparatus before it is measured at the shuttle gas pressure sensor 25, the receipt of balloon-based data is filtered and delayed relative to the receipt of fiber optic data, which is transmitted optically and is received instantaneously in comparison to the data from the balloon. The relative delay between the balloon-based data and the fiber optic data is calculated and then used to time-align the balloon-based data and fiber optic data such that the two types of data can be properly compared.

In order to determine the relative delay between the balloon-based data and the fiber optic data, a correlation is performed between a two second window of the balloon-based data and the corresponding two second window of the fiber optic data. FIG. 5B shows the results of such a correlation performed on the FIG. 5A data. As can be seen from FIG. 5B, the best time alignment occurs at a point in time corresponding to the peak of the correlation function, i.e. when the data from the fiber optic sensor is delayed by 17 sampling periods (68 msecs) relative to the data received through the balloon. Accordingly, the correlation indicates that the shuttle gas system delays receipt of the balloon-based data by 17 sampling periods relative to receipt of the fiber optic data. Of course, the 17 sample delay was computed for a particular test system under particular conditions and the delays for various embodiments of the invention may vary, as may the delays computed for a particular embodiment under various conditions.

Figure 6A:
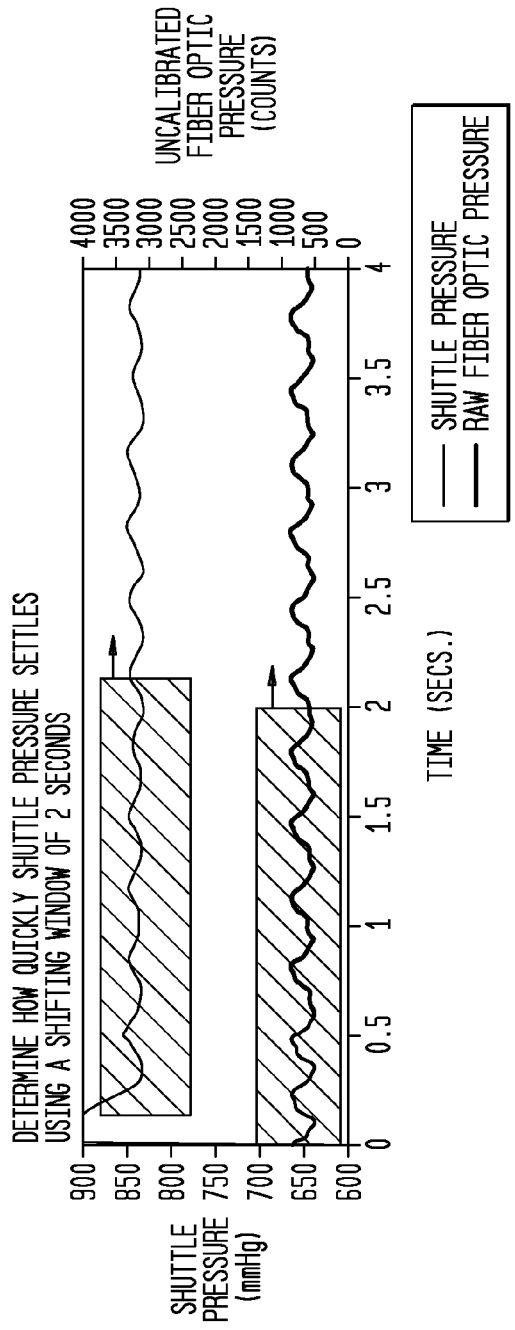
FIGS. 6A and 6B are graphs showing how correlation is used to determine the low-pass filtering effect of an IAB system on blood pressure measurements obtained through the IAB system balloon.
Figure 6B:
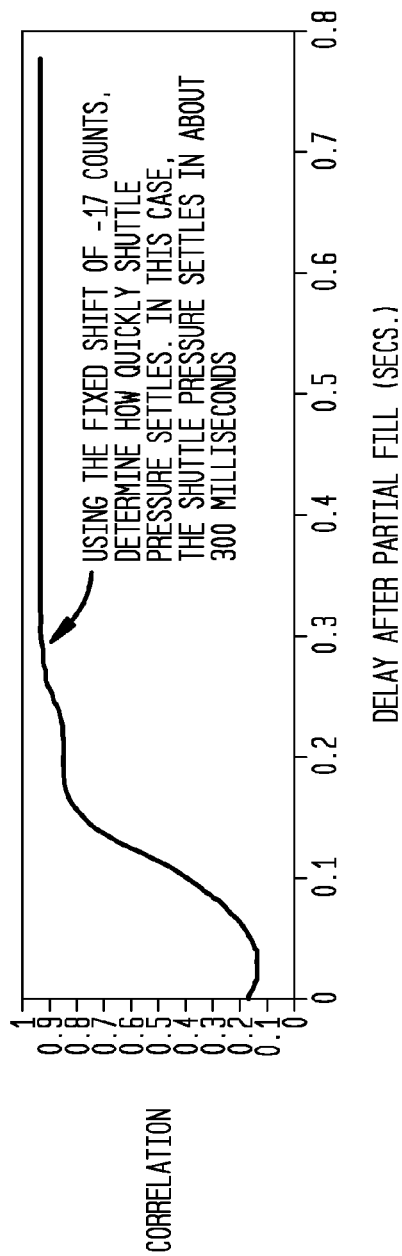

As noted previously, the geometry of the shuttle gas system has a low pass filtering effect on the balloon-based pressure measurements, i.e. it functions as a "de-facto" low-pass pneumatic filter. As a result, the frequency spectra of the shuttle gas pressure signal and the fiber optic pressure signal differ. Higher calibration accuracy is achieved if the two spectra are "equalized." Equalization is achieved by filtering the fiber optic signal so that it is spectrally similar to the shuttle gas signal. In a preferred embodiment, a correlation method is used to estimate the break frequency of the low-pass filtering effect of the IAB system on blood pressure measurements obtained through the IAB system balloon. That is, time required for the shuttle gas channel to settle to equilibrium after the IAB is inflated is used to estimate the magnitude of the pneumatic filter's effect on the shuttle gas signal; and the settling time is measured using a correlation technique wherein the shuttle gas and fiber signals are correlated and the correlation values are examined to determine when the shuttle gas channel has settled to equilibrium. Such correlation technique is illustrated in FIG. 6A. In FIG. 6A, a cross-correlation using conventional techniques is performed between the initial two second window of fiber optic data, collected immediately after the membrane is toggled to partially inflate the balloon, and the corresponding two second window of balloon-based data collected immediately after the membrane is toggled to partially inflate the balloon. The window of fiber optic data is shifted to the right (delayed) by the 17 sample delay previously computed to account for the delay on balloon-based measurements imparted by the shuttle gas system. The results of the correlation of FIG. 6A are shown in FIG. 6B. As can be seen in FIG. 6B, the correlation appears to stabilize at about t=0.3 seconds. The time at which the correlation stabilizes (0.3 seconds) is an indirect measure of the effect of the pneumatic filter upon the shuttle gas waveform.

The time at which the correlation stabilizes is used to design a filter having characteristics matching those of the estimated pneumatic filter. The filter designed according to the settling time is applied to the fiber optic signal. The filter can be designed using any of the well-known methods of filter design.

It should be noted that the FIG. 6B filter characteristic of t=0.3 seconds was computed for a particular test system under particular conditions and the characteristics computed for various embodiments of the invention may vary, as may the characteristics computed for a particular embodiment under various conditions. In any case, a filter that simulates that simulates the filtering effect of the shuttle gas system is designed.

Thus, the invention addresses the delay and filtering issues by: (1) estimating the relative time delay between the shuttle gas and fiber optic signal paths, and re-aligning the shuttle gas and fiber optic signals compensate for the relative delay; and (2) estimating the filtering effect of the pneumatic pathway upon the shuttle gas signal and then applying a computational filter with similar characteristics to the fiber optic signal in order to equalize the frequency spectra of the shuttle gas signal and fiber optic signal.

Figure 7:
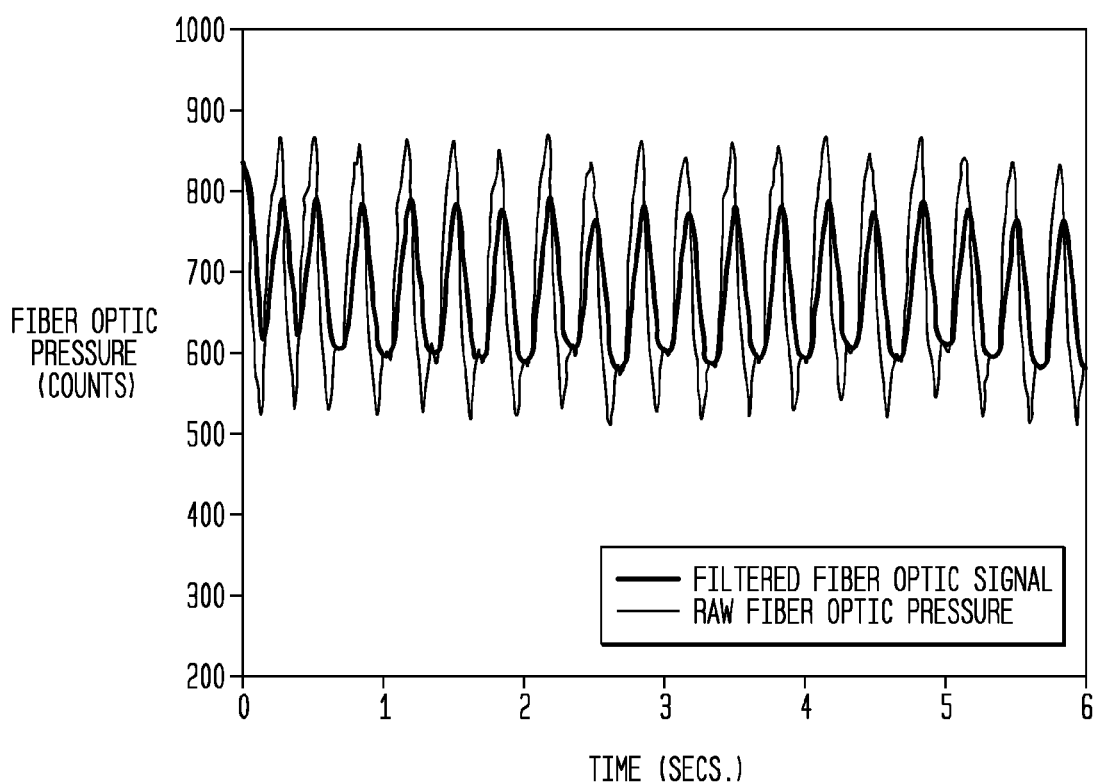
FIG. 7 is a graph showing a blood pressure signal obtained from an IAB system fiber optic sensor and the same signal after is has been passed through a filter designed to simulate the filtering effect of the IAB system pneumatics on blood pressure measurements obtained through the IAB system's balloon.

In any event, once the filtering characteristic of the shuttle gas system has been determined and a filter has been designed to simulate the filtering effects of the shuttle gas system, the fiber optic data is filtered so that it can be compared to the balloon-based data apart from the filtering effects of the shuttle gas system. However, such filter also has an associated delay. FIG. 7 is a graph showing the blood pressure signal obtained from the fiber optic sensor during the data collection period and the same signal after being passed through a filter designed to simulate the filtering effect of the shuttle gas system. As can be seen from FIG. 7, the filtering performed on the fiber optic data imparts a time shift (or "phase shift") to the filtered data. Accordingly, to properly account for the filtering effects of the shuttle gas system when comparing fiber optic data to balloon-based data, the fiber optic data must be time-shifted after filtering such that the filtered fiber optic data will be in phase with the balloon-based data.

Figure 8A:
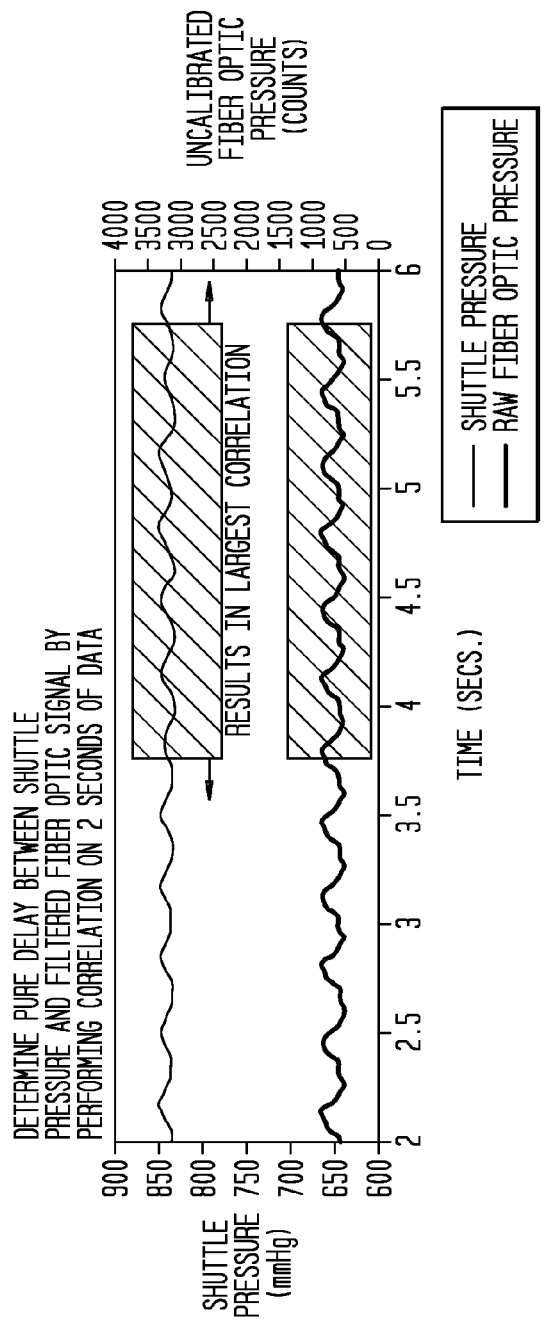
FIGS. 8A and 8B are graphs showing how correlation is used to determine the relative time delay between blood pressure measurements obtained through an IAB system's balloon and blood pressure measurements obtained from a fiber optic sensor associated with the balloon, wherein the measurements obtained from the fiber optic sensor have been filtered.
Figure 8B:
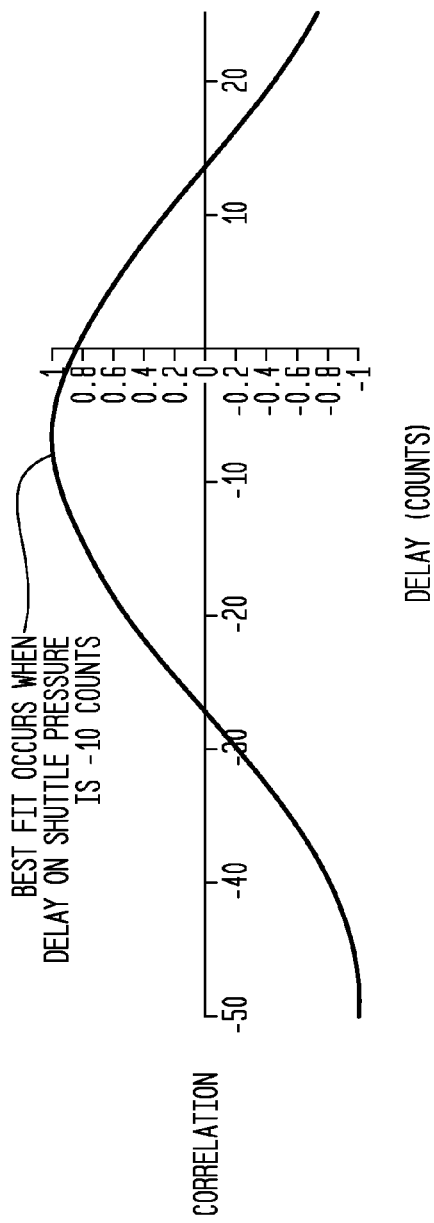

FIGS. 8A and 8B are graphs showing how correlation is used to determine the relative delay between the balloon-based blood pressure measurements and the filtered fiber optic blood pressure measurements. FIG. 8A shows seconds two through six of the balloon-based data and the filtered fiber optic data. The fiber optic data has been filtered to simulate the filtering effect of the shuttle gas system. In order to determine the relative delay between the balloon-based data and the filtered fiber optic data, a conventional correlation is performed between a two second window of the balloon-based data and the corresponding two second window of filtered fiber optic data. FIG. 8B shows the results of the correlation performed on the FIG. 8A data. As can be seen from FIG. 8B, the best fit occurs when the filtered fiber optic data is delayed by 10 sampling periods, or "counts," relative to the data received through the balloon. Of course, the 10 sample delay was computed for a particular test system under particular conditions and the delays computed for various embodiments of the invention may vary, as may the delays computed for a particular embodiment under various conditions.

Figure 9:
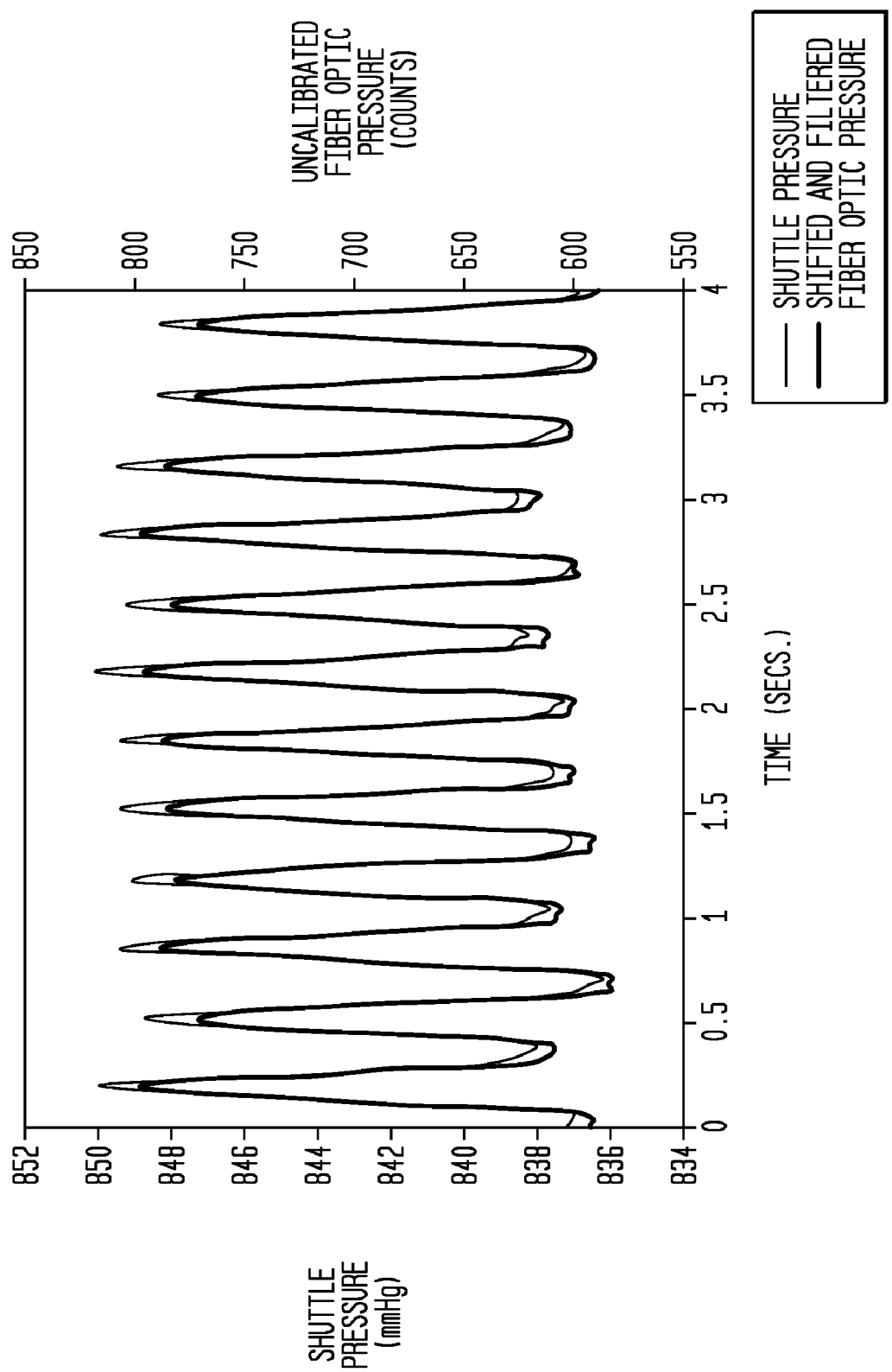
FIG. 9 is a graph showing a blood pressure signal obtained through an IAB system balloon and a blood pressure signal obtained from a fiber optic sensor associated with the balloon, wherein the signal obtained from the fiber optic sensor has been filtered and shifted to align them in time.

Once the appropriate filtering and shifting has been applied to the fiber optic calibration data, the fiber optic data can be compared to the balloon-based calibration data FIG. 9 is a graph showing the blood pressure signal obtained through the IAB balloon and the blood pressure signal obtained from the fiber optic sensor after appropriate filtering and shifting.

In a preferred embodiment, the amplitude of seconds 2 through 6 of the balloon pressure data and the shifted, filtered fiber optic pressure data are independently sorted. This sorting process minimizes non-linear effects that may appear on the balloon pressure and ensures a matching of the "nth-largest" value of the balloon-based data to the "nth-largest" value of the fiber optic data where n ranges from 1 to the number of samples recorded for each type of data. That is, the balloon-based data and fiber optic data are rank ordered from maximum to minimum.

Further, in a preferred embodiment, an exclusion process is performed on the sorted data. More specifically, after the two types of data have been sorted, an equal number of extreme values are dropped from the "top" and "bottom" of each ranked list. That is, only the "middle" portions of the ranked lists are considered.

FIG. 9A shows a simplified example of how the sorting and exclusion processes work. The data values considered in the example is not consistent with the data values discussed in FIGS. 4-9. In FIG. 9A, six illustrative samples of balloon-based data and six illustrative samples of fiber optic data are plotted in a graph 110a of pressure vs. time. A table 110b lists the plotted samples in time order. In table 120b, the samples have been ranked from lowest value to highest value. Graph 120a is a pressure vs. rank graph depicting the ranked samples. The process by which the data of 110a and 110b is transformed into the data of 120a and 120b is the sorting process. The exclusion process is depicted in graph 130a and table 130b. Graph 130a is a graph of balloon-based data vs. fiber optic data, and it highlights the extreme points that are eliminated by the exclusion process. Table 130b is the same as table 120b, with the exception that the points eliminated by the exclusion process are highlighted.

The sorting and exclusion processes have two beneficial effects. First, extreme points ("outliers") are excluded from the calibration process. Second, data points from the peaks and valleys of the blood pressure waveform are excluded from the calibration process. In particular, the processes exclude data which is most likely to be corrupted by the poor fidelity of the shuttle gas sensor.

It should be noted that the sorting and exclusion processes are optional features of the invention and the invention may be practiced without such features.

Figure 10:
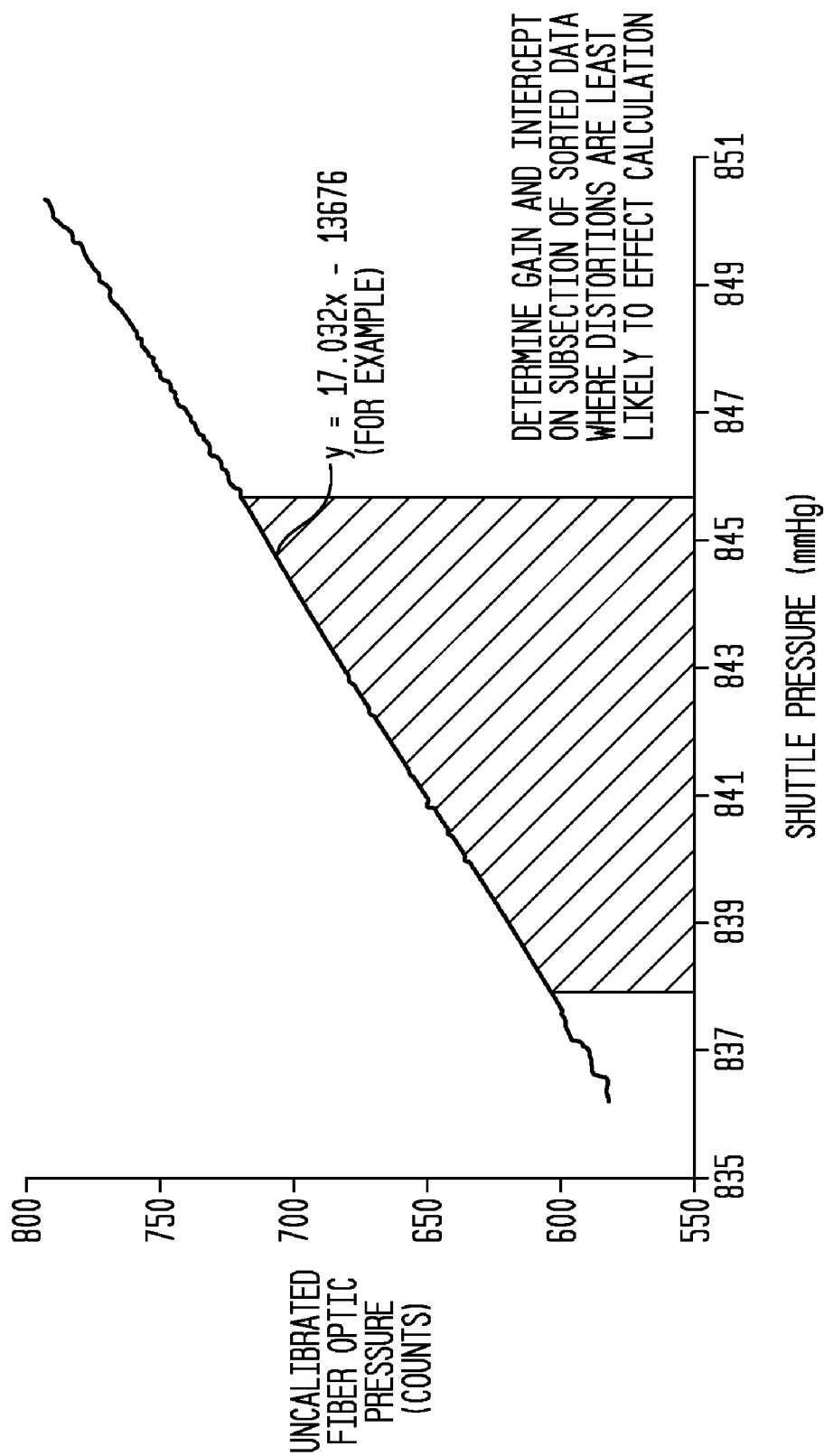
FIG. 10 is a graph showing the relationship between a blood pressure signal obtained through an IAB system balloon and a blood pressure signal obtained from a fiber optic sensor associated with the balloon, wherein the signal obtained from the fiber optic sensor has been filtered and time-shifted, and wherein both the data representing the balloon-based signal and the data representing the fiber optic signal have undergone both sorting and exclusion processes.

Referring now to FIG. 10, the data values considered in FIGS. 4-9 are once again considered. FIG. 10 is a graph showing the relationship between the two signals depicted in FIG. 9 after a sorting process has been performed on the FIG. 9 data. FIG. 10 also shows how a linear function is used to approximate the relationship between the two signals. The FIG. 10 graph has been created with the abscissa representing the sorted blood pressure signal obtained through the IAB system balloon and the ordinate representing the sorted, filtered and shifted fiber optic signal. The calibration values are determined by taking a sub-region of the data (for instance the $100^{th}$-$400^{th}$ values). The line that best fits this sub-region of data is shown in FIG. 10. In this example, one can use the equation describing the straight line of FIG. 10 (y=17.032x−13676) to compute calibrated fiber optic sensor readings from raw fiber optic sensor readings. More specifically, raw fiber optic measurements are converted to a calibrated pressure measurement by using the equation shown in FIG. 10. Of course, the equation is applied as x=(y+13676)/17.032; wherein "x" is the calibrated fiber optic measurement, and "y" is the filtered and delayed fiber optic measurement.

It is noted that the use of a straight line to describe the data plotted in FIG. 10 is merely illustrative. Many alternative techniques may be employed without departing from the spirit and scope of the invention. For example, a curve may be used to describe the data plotted in FIG. 10, in which case one of the well-known curve-fitting algorithms may be used to generate an equation describing a curve that fits the data. The process of developing a mathematical expression to describe the data depicted in FIG. 10 may be referred to as "regression."

Having provided a detailed description of a preferred embodiment of the calibration process of the invention, some additional considerations will now be discussed in detail.

Regarding the shuttle gas system's effect on balloon-based measurements, it is important to note that a pressure change incident on an IAB must propagate through a volume of gas before being detected by the shuttle gas pressure sensor. By minimizing the volume of gas through which a pressure change must propagate, the calibration accuracy can be improved.

In order to understand how minimizing the propagation volume improves calibration, consider the application of a pressure waveform in the form of a "step" to the exterior membrane of a flaccid IAB. The "step" is an instantaneous jump in pressure from one constant value to another. If it is assumed that prior to the step the pressure of the shuttle gas is constant and in equilibrium, equilibrium meaning that the shuttle gas pressure is the same at all points within the shuttle gas system, upon application of the step in external pressure, the increase in external pressure temporarily upsets the equilibrium of the shuttle gas.

More specifically, higher pressure on the exterior of IAB membrane crushes the balloon and thereby reduces its volume. The IAB loses volume until the pressure within it is nominally equal to the external pressure. This process occurs very rapidly, and very quickly the pressure inside the IAB is equal to the externally applied pressure. However, the system is not yet in pressure equilibrium. Due to the higher pressure inside the IAB, gas flows out of the IAB, through the indwelling catheter and to the volumes of the extension catheter, safety disk and IABP console.

As gas flows from the IAB, the IAB volume is further reduced due to the flow of gas from it. The amount of volume loss depends upon the total volume of the IAB system. (In the limit, it is possible for an increase in external pressure result in a completely deflated IAB, i.e. if the pressure increase is large or if the system volume is large.) During this dynamic interval, the flow of shuttle gas through the restrictive indwelling catheter results in a pressure drop. This drop is present until the gas flow stops, i.e. when the pressure of gas outside the IAB is equal to the pressure in the IAB. At this point, equilibrium is once again established. The time required to reach equilibrium is proportional to the magnitudes of the system volume and the resistance-to-flow of the indwelling catheter. As they get larger, the time required to achieve equilibrium gets longer.

Throughout the process of regaining equilibrium the shuttle gas pressure is monitored by the shuttle gas pressure sensor. Due to the dynamic effect of the step waveform upon the shuttle gas, the sensor's reading differs from the pressure in the IAB until the shuttle gas has transitioned to a new equilibrium point. That is, the pressure seen by the sensor is not a step. Instead, the pressure exponentially approaches the equilibrium value. Accordingly, the system volume and catheter resistance have the function of a low pass filter, the fast moving features in the patient's blood pressure being attenuated. FIG. 11 shows several graphs superimposed on an IAB system similar to that of FIG. 1. The graphs of FIG. 11 show how the pressure changes at various points in the system when the system experiences a "step" in blood pressure.

Figure 12A:
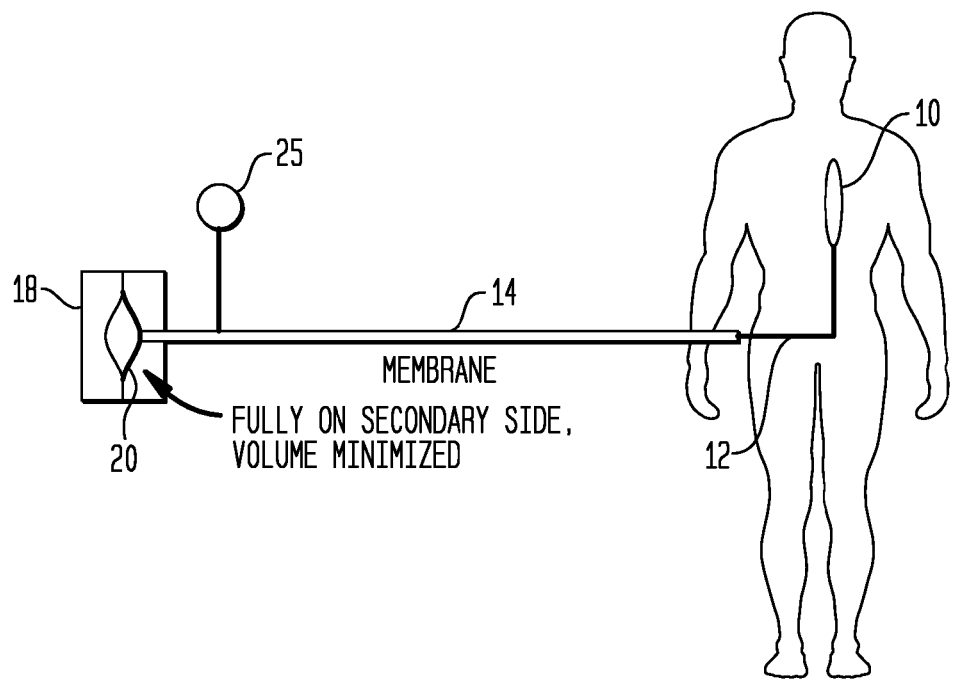
FIGS. 12A and 12B show how a reduction in system gas volume is achieved through positioning of an IAB system isolator membrane, FIG. 12A showing the membrane fully on the secondary side of the isolator, and FIG. 12B showing the membrane fully on the primary side of the isolator.
Figure 12B:
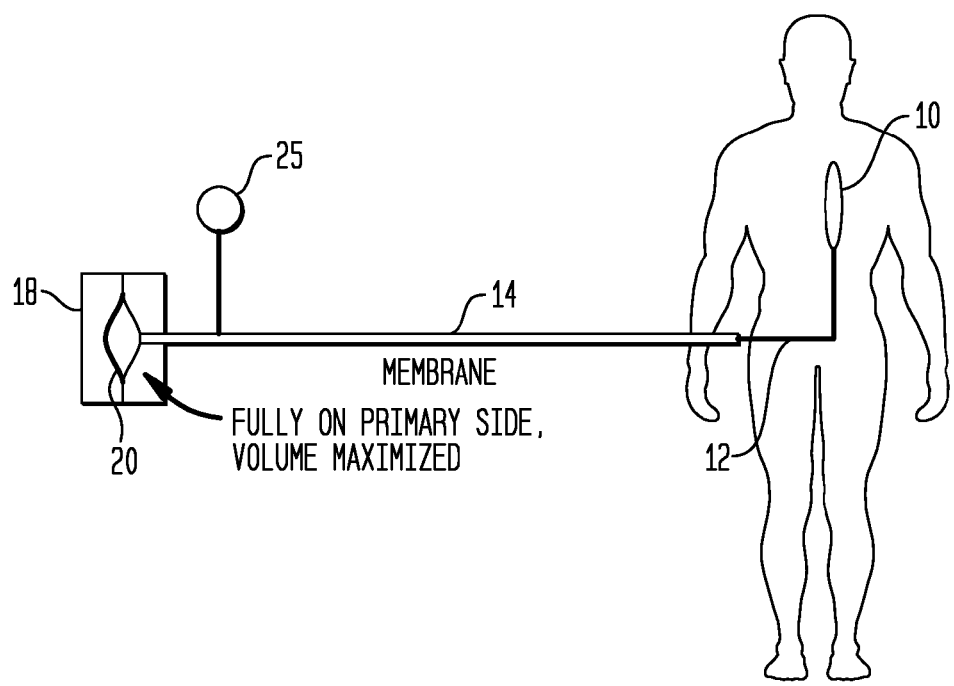

The bandwidth of balloon-based measurements can be improved by reducing catheter resistance and/or reducing the volume of shuttle gas through which pressure changes must propagate before being detected by the shuttle gas pressure sensor. Catheter resistance can be reduced by increasing its diameter. However, for clinical reasons, it is preferable to keep the catheter's diameter small The shuttle gas volume can be reduced by a number of means. Extension catheter dead volume can be reduced by reducing its length and diameter. However, clinical and practical considerations limit the magnitude of these changes. Shuttle gas volume can be minimized during the calibration process by assuring that the isolator volume is minimized during calibration. This can be achieved, if the isolator's membrane is placed fully on the secondary side of the isolator during calibration. The reduction in system gas volume achieved by placing the isolator membrane on the secondary side is illustrated in FIGS. 12A and 12B. FIG. 12A shows the membrane fully on the secondary side of the isolator and FIG. 12B shows the membrane fully on the primary side of the isolator.

Figure 13:
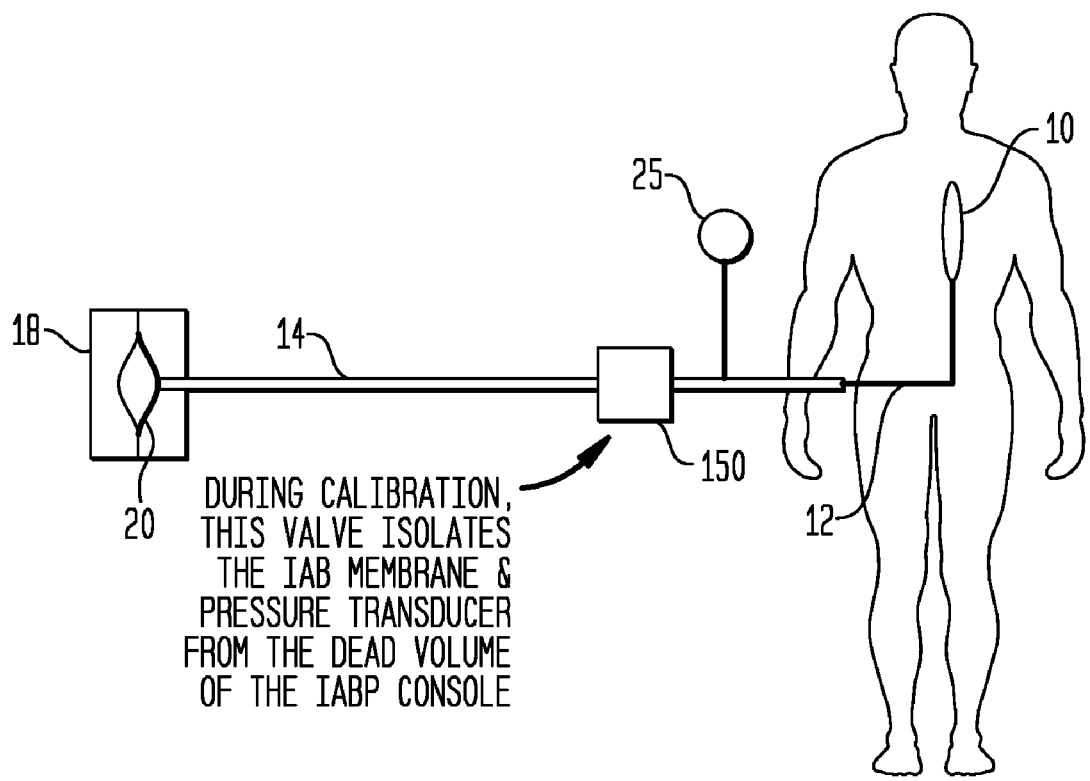
FIG. 13 shows an IAB system that includes a series valve for isolating a shuttle gas pressure sensor from a portion of the system extender and from the system isolator.

Alternatively, the IAB and shuttle gas pressure sensor can be temporarily isolated from the other volumes in the IAB system via a series valve. FIG. 13 shows such a system. In FIG. 13, a series valve 150 is placed in the extender path and isolates sensor 25 from a portion of the extender and the isolator.

Another alternative is to provide a separate gas lumen for the purpose of sensing pressure in the IAB, i.e. the pressure drop in the indwelling catheter is not seen by the separate sensing lumen. FIG. 14 shows such a system. In FIG. 14, a sensing lumen 160 couples the IAB directly to the shuttle gas pressure sensor 25. This assumes that the pressure sensor and sensing lumen have low dead volume, and that the sensing lumen is not pneumatically restrictive (its diameter is not excessively small). FIG. 14 includes several graphs illustrating how the pressure changes at various points in the FIG. 14 system when the system experiences a "step" in blood pressure.

Although the invention herein has been described with reference to particular embodiments, it is to be understood that these embodiments are merely illustrative of the principles and applications of the present invention. It is therefore to be understood that numerous modifications may be made to the illustrative embodiments. For example, rather than partially inflating the balloon to read blood pressure during calibration, the balloon can be fully inflated to read blood pressure during calibration. Still other arrangements may be devised without departing from the spirit and scope of the present invention as set forth in the following brief statements of certain preferred embodiments of the invention.

The invention claimed is:

1. A method for performing an in-vivo calibration of a blood pressure sensor that is associated with a balloon of an in-vivo balloon system, the sensor and balloon being associated such that the sensor is in-vivo when the balloon is in-vivo, the method comprising the steps of:
   inflating or deflating the balloon so that a gas pressure in the balloon system is indicative of a patient's blood pressure;
   monitoring the patient's blood pressure by observing the gas pressure through a gas pressure sensor while simultaneously monitoring the patient's blood pressure through the blood pressure sensor and recording a pressure signal generated by a gas pressure sensor and a pressure signal generated by the blood pressure sensor; and
   using blood pressure readings obtained by monitoring the gas pressure as reference blood pressure measurements and determining a mathematical relationship between blood pressure measurements obtained through the sensor and the reference blood pressure measurements such that future blood pressure measurements obtained through the sensor can be modified according to the mathematical relationship to generate calibrated blood pressure measurements,
   wherein the step of using includes performing a correlation function between a window of the balloon-based data and the corresponding window of the blood pressure sensor, and performing a time-alignment of the pressure signal generated by the gas pressure sensor and the pressure signal generated by the blood pressure sensor to a point in time corresponding to a peak of the correlation function.

2. A method for performing an in-vivo calibration of a blood pressure sensor that is associated with a balloon of an in-vivo balloon system, the sensor and balloon being associated such that the sensor is in-vivo when the balloon is in-vivo, the method comprising the steps of:

inflating the balloon so that a gas pressure in the balloon system is indicative of a patient's blood pressure;

monitoring the patient's blood pressure by observing the gas pressure through a gas pressure sensor while simultaneously monitoring the patient's blood pressure through the blood pressure sensor and recording a pressure signal generated by a gas pressure sensor and a pressure signal generated by the blood pressure sensor from the time where a membrane in the in-vivo balloon system is toggled to inflate the balloon; and using blood pressure readings obtained by monitoring the gas pressure as reference blood pressure measurements and determining a mathematical relationship between blood pressure measurements obtained through the sensor and the reference blood pressure measurements such that future blood pressure measurements obtained through the sensor can be modified according to the mathematical relationship to generate calibrated blood pressure measurements, wherein the step of using includes filtering the pressure signal generated by the blood pressure sensor to generate a filtered signal and using a correlation or cross-correlation function on the filtered signal and the pressure signal generated by the gas pressure sensor to determine a relative time delay between the filtered signal and the pressure signal generated by the gas pressure sensor, and generating a filtered and time-shifted signal by time-shifting the filtered signal to compensate for the relative time delay.

3. The method as recited in claim 2, wherein the pressure signal generated by the gas pressure sensor, the pressure signal generated by the blood pressure sensor, and the filtered and time-shifted signal are made up of periodic samples, and the step of using includes performing a sorting process based on amplitudes of the pressure signal generated by the blood pressure sensor and the filtered and time shifted signal over the same time-shifted period.

4. A method for performing an in-vivo calibration of a blood pressure sensor that is associated with a balloon of an in-vivo balloon system, the sensor and balloon being associated such that the sensor is in-vivo when the balloon is in-vivo, the method comprising the steps of:

inflating or deflating the balloon so that a gas pressure in the balloon system is indicative of a patient's blood pressure;

monitoring the patient's blood pressure by observing the gas pressure while simultaneously monitoring the patient's blood pressure through the sensor and recording a pressure signal generated by a gas pressure sensor and a pressure signal generated by the blood pressure sensor;

correlating the pressure signal generated by the blood pressure sensor and the pressure signal generated by the gas pressure sensor to determine a relative time delay between the pressure signal generated by the blood pressure sensor and the pressure signal generated by the gas pressure sensor; and using blood pressure readings obtained by monitoring the gas pressure as reference blood pressure measurements and determining a mathematical relationship between blood pressure measurements obtained through the sensor and the reference blood pressure measurements such that future blood pressure measurements obtained through the sensor can be modified according to the mathematical relationship to generate calibrated blood pressure measurements, wherein the step of using includes generating a time-shifted signal by time-shifting the pressure signal generated by the blood pressure sensor to compensate for the relative time delay, and wherein the pressure signal generated by the gas pressure sensor, the pressure signal generated by the blood pressure sensor, and the time-shifted signal are made up of periodic samples, and the step of using includes performing a sorting process based on amplitudes of the pressure signal generated by the gas pressure sensor and the time shifted signal over the same time-shifted period.

5. The method of claim 4, wherein the sorting process removes data corresponding to maximum and minimum amplitudes.

6. The method of claim 5, wherein the maximum and minimum amplitudes can be individually removed from the time-shifted signal or the pressure signal generated by the gas pressure sensor or both of these signals.

7. The method of claim 4, wherein the step of using further includes filtering the pressure signal generated by the blood pressure sensor to generate a filtered signal using a filter that simulates the effect of the balloon system configuration upon the gas pressure as reflected in the pressure signal generated by the gas pressure sensor, and the sorting process is performed based on amplitudes of the pressure signal generated by the blood pressure sensor and filtered and time shifted fiber optic pressure signal over the same period.

* * * * *